(12) United States Patent
Sarnago Andía et al.

(10) Patent No.: US 11,224,744 B2
(45) Date of Patent: Jan. 18, 2022

(54) ELECTRONIC MODULAR SYSTEM WITH VARIABLE POWER FOR GENERATING ELECTRICAL PULSES AND ASSOCIATED USES THEREOF

(71) Applicants: UNIVERSIDAD DE ZARAGOZA, Saragossa (ES); UNIVERSITAT POMPEU FABRA, Barcelona (ES); STERLING MEDICAL DEVICES, Moonachie, NJ (US)

(72) Inventors: Hector Sarnago Andía, Saragossa (ES); Óscar Lucía Gil, Saragossa (ES); José Miguel Burdío Pinilla, Saragossa (ES); Alejandro Naval Pallarés, Saragossa (ES); Antoni Ivorra Cano, Barcelona (ES); Quim Castellví Fernández, Barcelona (ES); Lawrence Bischoff, Denville, NJ (US)

(73) Assignees: UNIVERSIDAD DE ZARAGOZA, Saragossa (ES); UNIVERSITAT POMPEU FABRA, Barcelona (ES); STERLING MEDICAL DEVICES, Moonachie, NJ (US)

( * ) Notice: Subject to any disclaimer, the term of this patent is extended or adjusted under 35 U.S.C. 154(b) by 0 days.

(21) Appl. No.: 16/867,960

(22) Filed: May 6, 2020

(65) Prior Publication Data

US 2020/0261718 A1 Aug. 20, 2020

Related U.S. Application Data

(63) Continuation-in-part of application No. 16/065,292, filed as application No. PCT/ES2016/070926 on Dec. 22, 2016, now Pat. No. 10,673,347.

(30) Foreign Application Priority Data

Dec. 22, 2015 (ES) ................................ ES201531870

(51) Int. Cl.
*A61N 1/32* (2006.01)
*A61B 18/12* (2006.01)
(Continued)

(52) U.S. Cl.
CPC .......... *A61N 1/327* (2013.01); *A61B 18/1206* (2013.01); *A23L 3/32* (2013.01);
(Continued)

(58) Field of Classification Search
CPC ................ A61N 1/327; A61B 18/1206; A61B 2018/005777; A61B 2018/1266;
(Continued)

(56) References Cited

U.S. PATENT DOCUMENTS 6,939,347 B2 9/2005 Thompson
9,124,182 B2 9/2015 Chen et al.
(Continued)

FOREIGN PATENT DOCUMENTS

WO 2011/017802 A1 2/2011

OTHER PUBLICATIONS

Bae et al., "High-Power Pulse Generator With Flexible Output Pattern," *IEEE Transactions on Power Electronics* 25(7):1675-1684, Jul. 2010.
(Continued)

*Primary Examiner* — Emily P Pham
(74) *Attorney, Agent, or Firm* — Seed Intellectual Property Law Group LLP

(57) ABSTRACT

The disclosure relates to variable power modular electronic systems for generating unipolar and bipolar electrical pulses and associated uses thereof. In an embodiment, such a system includes one or more pulse generators for generating electrical pulses that can be connected in series; a charging circuit for charging the pulse generators; and a controller communicatively coupled to the pulse generators and the
(Continued)

charging circuit. Advantageously, each pulse generator may include an AC/DC rectifier and a DC/AC inverter connected to said AC/DC rectifier in a bridge configuration to generate bipolar output electrical pulses or pulse trains. In addition, the charging circuit may include a DC/DC step-up converter connected to an indirect DC/AC inverter. The system provided in various embodiments of the disclosure also provides a great versatility for adaptation to various applications and high output voltage and current values.

21 Claims, 7 Drawing Sheets

(51) Int. Cl.
*A61B 18/00* (2006.01)
*A23L 3/32* (2006.01)
(52) U.S. Cl.
CPC ... *A23V 2002/00* (2013.01); *A61B 2018/0075* (2013.01); *A61B 2018/00577* (2013.01); *A61B 2018/126* (2013.01); *A61B 2018/1253* (2013.01); *A61B 2018/1266* (2013.01)
(58) Field of Classification Search
CPC ...... A61B 2018/1253; A61B 2018/126; A61B 2018/0075; A61B 2018/00726; A61B 2018/1286; A23V 2002/00; A23L 3/32
See application file for complete search history.

(56) References Cited

U.S. PATENT DOCUMENTS

| | | |
|---|---|---|
| 2004/0076028 A1 | 4/2004 | Achleitner et al. |
| 2005/0190586 A1 | 9/2005 | Radzinski et al. |
| 2008/0055941 A1 | 3/2008 | Victor et al. |
| 2008/0266919 A1 | 10/2008 | Mallwitz |
| 2009/0052214 A1 | 2/2009 | Edo et al. |
| 2010/0309702 A1 | 12/2010 | Yuan et al. |
| 2011/0175579 A1 | 7/2011 | Mazumdar |
| 2012/0281441 A1 | 9/2012 | Orszulak et al. |
| 2012/0239026 A1 | 11/2012 | Liu et al. |
| 2015/0230864 A1 | 8/2015 | Xuan et al. |
| 2016/0329875 A1 | 11/2016 | Song et al. |
| 2017/0080222 A1 | 3/2017 | Hayakawa et al. |
| 2018/0154142 A1 | 6/2018 | Guo et al. |

OTHER PUBLICATIONS

Bernal et al., "A Review of Pulse Generation Topologies for Clinical Electroporation," IECON 2015—41$^{st}$ Annual Conference of the IEEE Industrial Electronics Society, Nov. 9-12, 2015, pp. 000625-000630.
International Search Report dated Mar. 28, 2017, for International Application No. PCT/ES2016/070926, 2 pages.
Redondo et al., "Analysis of a modular generator for high-voltage, high-frequency pulsed applications, using low voltage semiconductors (<1 kV) and series connected step-up (1:10) transformers," *Review of Scientific Instruments* 78, 034702, 2007, 8 pages.
Varma et al., "Development of a Solid State Versatile Pulsar for High Voltage and High Power Applications," IEEE Pulsed Power Conference, 2009, pp. 1312-1316.

ELECTRONIC MODULAR SYSTEM WITH VARIABLE POWER FOR GENERATING ELECTRICAL PULSES AND ASSOCIATED USES THEREOF

BACKGROUND

Technical Field

The present disclosure relates to the technical field of electroporation devices used in medical treatments to improve absorption of medicines or destruction of tumor cells. More specifically, the disclosure relates to a modular electronic system with variable power for generating unipolar and bipolar electrical pulses. The field of greatest interest in the disclosure is biomedicine, although it is also applicable in other fields, such as for sterilization in the food industry.

Description of the Related Art

Electroporation is a technique used in medicine which involves applying a pulsed electric field to a living organism such that changes at a cell membrane level are triggered, which can be permanent or temporary depending on the strength of the applied field.

These electrical pulses are produced by generators with various characteristics depending on the desired electroporation technique or problem to treat. When the voltage across a plasma membrane exceeds the dielectric strength thereof, pores are formed which can close after some time. If the pore openings are temporary and reversible it is possible to introduce extracellular compounds in the cell interior for therapeutic purposes. Alternatively, the pores can remain open irreversibly, resulting in cell death by apoptosis. In this context the reversibility of the technique and the size and duration of the pores depend on the strength of the electric field applied and the exposure time of the cell to the same.

Irreversible electroporation (IRE) is a non-thermal ablation technique that is currently of great interest in the treatment of certain highly resistant tumors. It consists in applying strong electric fields to open tissue cell membranes and cause cell death. Some advantages of this technique over traditional tumors ablation techniques are the possibility of treating areas near major vessels, as these are not affected by thermal cooling, or the preservation of connective tissue, vessels and other ducts. To achieve irreversibility in the electroporation technique the generator must reach high voltages and currents, with a threshold that depends on the type of cells to be treated.

Currently available unipolar pulse generators for medical applications have insufficient maximum voltage levels for an efficient generalized use in electroporation techniques. This is the case for example with the system disclosed in Review of Scientific Instruments 78, 034702 (2007), in the article "Analysis of a modular generator for high-voltage, high-frequency pulsed applications, using low voltage semiconductors (1 kV) and series connected step-up (1:10) transformers" (L. M. Redondo et al.), which describes a modular generator that produces unipolar pulses that despite having a high voltage fall short of the voltage levels required for the applications considered herein. A similar case is the system disclosed in patent application WO 2011/017802 A1 (S. Jayaram et al.), which describes an electrical generator with a plurality of modules connected in cascade, and which generates unipolar pulses with variable output voltages depending on the number of modules included in the system.

In this way, although known modular generators allow solving some of the drawbacks of traditional techniques, there is a limit to the maximum voltages and currents attainable, and present several restrictions regarding the duration and configurability of the pulses generated, hindering their use in the field of irreversible electroporation of tumor cells.

In addition, existing generators used in irreversible electroporation that can provide the necessary output voltages and currents are however not too versatile, providing a limited range of voltages and limiting their use to certain specific types of cell or situations.

In view of the above, there is a need in the technical field for alternatives that allow solving the issues described above, reaching output voltage and current values suitable for a generalized use in irreversible electroporation, while providing devices that can be adapted for use in a large variety of situations or medical applications.

BRIEF SUMMARY

In various embodiments, the present disclosure provides a pulse generator technology based on a module structure and unipolar or bipolar pulses providing greater versatility and higher output voltage that generators of the prior art. In some embodiments, a high-voltage generator is provided based on a modular, versatile electronic system for power generation that comprises a control unit and allows adapting the strength and other characteristics of the electrical pulses to each specific application according to the number of modules used. Said generator may be preferably used in electroporation, and can be adapted to various specific problems or organs due to the versatility of the modular system and the possibility of attaining high voltages and currents.

The present disclosure provides, in one or more embodiments, a system comprising:

One or more electrical pulse generation modules, where said modules can be connected in series or in parallel. In connection in series, the output voltage of the pulses is the sum of the individual output voltages of each module. In connection in parallel, the total current is the sum of the currents of each module.

A charging unit for the generation modules.

A control unit for the generation modules and the charging unit.

Advantageously, the generation modules are coupled by isolation transformers to the charging unit, where said charging unit is arranged as the primary side of the transformers and the generation modules are arranged as the secondary side of the transformers.

In addition, each generation module preferably comprises an AC/DC rectifier at the output of the corresponding transformer, and a DC/AC inverter connected to said AC/DC rectifier, configured as a bridge for generating output electrical pulses or pulse rains, and the charging unit comprises a DC/DC step up converter connected to an indirect DC/AC inverter, where said DC/AC inverter is connected to the input of the transformer primary side.

This allows both obtaining a higher voltage and current in the pulses due to their bipolar character, and adding modules in series and in parallel to the device architecture, which in turn provides a technical solution that increases the versatility of the devices. In addition, bipolar pulses are obtained in the present disclosure by the bridge configuration of the inverter inside each generation module.

More specifically, the generator of the disclosure allows obtaining pulses with high voltages (on the order of 10-15 kV peak to peak) and currents (400-600 A peak to peak), greatly exceeding those of currently available generators used in clinical applications, providing in medical applications more than twice the voltage and five times the current obtained by technologies available in the market. This means that the generator of the disclosure allows reaching ablation volumes much higher than those available at this time and that, since no low-frequency transformer is used, a more compact and lightweight solution is obtained than that provided by current generators.

In addition, the modular design proposed by the system of the disclosure allows using the number of modules required to reach the desired voltage for a given application. This increases versatility of the output voltage with unipolar or bipolar pulses or pulse trains with a fully configurable width (from 1 µs) and number of pulses. This configurability implies the following technical advantages:

Attenuating the effect of electrochemical reactions. These reactions are harmful to both the electrodes and organic tissues.

Elimination of hydrogen and oxygen bubble formation due to hydrolysis.

Lower neurostimulation leading to unwanted muscle activation.

Possibility of applying quick bursts of short pulses, significantly reducing the total time of treatment.

An additional advantage is that the system of the disclosure does not require the use of an output transformer. This means a key difference, as it allows obtaining much lower output impedance that is therefore less influenced by the load. This aspect has great importance in electroporation, as both the electrodes and the tissue to connect lead to a highly variable load. In this way the disclosure can always guarantee a square voltage form at the output.

In a embodiment of the disclosure, one or more pulse generator modules comprise an auxiliary AC/DC block powered by the output of the isolation transformer and also connected to the AC/DC rectifier and the DC/AC inverter, to generate a power supply voltage for the same. Analogously, the charging unit may include an auxiliary DC/DC block, connected to the DC/DC step-up converter and the indirect DC/AC inverter, to generate a power supply voltage for the same.

In another embodiment of the disclosure, the frequency of the indirect DC/AC inverter of the charging unit is 200 kHz or higher, and the insulation voltage of the transformers may be 15 kV or higher.

In another embodiment of the disclosure, the generator includes a control architecture based on a programmable logic device (FPGA) that allows a full current and future implementation of advanced synchronization functions with ECG, protections, treatment automation, etc. This provides a greater versatility and adaptation of the output voltage pulses with respect to the treatment to be performed.

The control unit of the system of the disclosure also allows programming the number of generator modules active while the pulses are applied. This allows changing quickly the magnitude of the applied pulses or pulse trains, thereby configuring the shape thereof (for example, pulses or pulse trains with ladder form can be applied). This is of interest, for example, in applications related to electroporation-assisted gene transfection (gene electrotransfer). In this field of application of electroporation it has been demonstrated that protocols consisting in a single short high-magnitude pulse followed by a longer low-magnitude pulse are more effective than protocols with two or more short high-magnitude pulses.

In another embodiment of the disclosure, the control unit comprises at least one connection to the generation modules and at least one connection to the charging unit, where these connections are insulated by optical fiber. This provides an improved insulation that increases the safety of use of the system.

In another embodiment of the disclosure, the generator is powered by batteries instead of by direct connection to the power grid as those currently used, thereby improving safety and insulation during the use thereof and simplifying the approval of the device and compliance with electromagnetic compatibility regulations.

In another embodiment of the disclosure, the generator comprises a wireless communication subsystem by WiFi connection to a computer that allows configuring several parameters such as polarity, amplitude, number of pulses in each burst, number of bursts and repetition frequency. This possibility of wireless control considerably increases the safety and convenience of use.

Various embodiments of the present disclosure relate to the associated uses of the system, which comprise applications for sterilization of food, waste treatment, contamination control, treatment of metals or semiconductors, molecular biology tests, and/or medical or cosmetic treatments. In some embodiments, the uses of the system related to molecular biology tests, medical and/or cosmetic treatments comprise electroporation applications.

In another embodiment of the disclosure, the variable power modular electronic system for generating unipolar or bipolar electrical pulses, comprises two or more inter-connectable pulse generation modules electrically coupled to one another in parallel or in series. The two or more inter-connectable pulse generation modules, in use, generate the unipolar or bipolar electrical pulses such that when the two or more inter-connectable pulse generation modules are coupled to one another in series an output voltage is a sum of individual output voltages of each pulse generation module, and when the two or more inter-connectable pulse generation modules are coupled to one another in parallel a total output current is the sum of the current of each pulse generation module.

The system further comprises one or more isolated AC/DC rectifiers coupled directly or indirectly to electric mains and containing an isolation transformer. For example, at least one isolated AC/DC rectifier is coupled to electric mains by means of an isolation transformer.

Each of the pulse generation modules includes a DC/AC inverter having a bridge configuration and coupled to the AC/DC rectifier, such that DC/AC inverter in use, outputs the unipolar or bipolar electrical pulses.

The system further comprises a system controller programmed to control activation and deactivation of the pulse generation modules, for generating the unipolar or bipolar electrical pulses, and for varying at least one magnitude of the unipolar or bipolar electrical pulses.

In one embodiment, at least one pulse generation module includes an individually isolated AC/DC rectifier. In a preferred embodiment, each pulse generation module incorporates an isolated AC/DC rectifier.

In this disclosure, an isolated device like an AC/DC rectifier, is a device connected to other devices of the system by means of an isolation transformer, such that the transformer isolates galvanically the device. Isolation could be connected to mains or located on the high-frequency side. In the case of an AC/DC rectifier, the input of the rectifier is connected to the secondary side or output of the transformer, and the primary side or input of the transformer could be connected to the electric mains.

In a preferred embodiment, the system further comprises a charging circuit which, in use, charges or supplies power to the pulse generation modules, wherein the charging circuit is adapted to be fed from electric mains. The charging circuit, comprises a common isolated AC/DC rectifier in common for the pulse generation modules, such that the pulse generation modules are coupled to the common isolated AC/DC rectifier.

In a preferred embodiment, the system comprises a common isolated AC/DC rectifier in common for the pulse generation modules, and at least one step-up or step-down device coupled with the common isolated AC/DC rectifier, such that the pulse generation modules are coupled to the common isolated AC/DC rectifier by means of the step-up or step-down device.

The system further comprises one or more pulse controllers, which in use, control activation and deactivation of the DC/AC inverter.

In addition, at least one system controller is further programmed to communicate with the pulse controller and distribute instructions to the pulse generation modules and charging circuit.

In one embodiment, one or more system controllers are integrated into one or more pulse generation modules, In one embodiment a pulse controller and system controller are integrated into the same pulse generation module.

In one embodiment, the system controller is programmed such that the amplitude between sequential unipolar or bipolar pulses is variable based on the number of pulse generation modules that are activated by a controller during a given pulse. In addition, the duration between sequential unipolar or bipolar pulses is variable based on the activation timing pattern created by a controller.

In one embodiment, one or more parameters of the unipolar or bipolar electrical pulses includes at least one of a polarity, an amplitude, a number, or a repetition frequency of the unipolar or bipolar electrical pulses.

In one embodiment, the controller is programmed such that in event that one or more of the pulse generation modules is short-circuited, the remaining operable pulse generation modules are switched open to block the output.

Preferably, at least one pulse generation module incorporates a current monitoring device, which in use detect a short-circuit state of the pulse generation modules.

The variable power modular electronic system of this disclosure, is preferably configured for its use in electroporation applications.

DETAILED DESCRIPTION

A detailed description of the disclosure is provided below with reference to one or more embodiments thereof based on FIG. 1 of this document. Said embodiments are provided for purposes of illustrating the claimed disclosure and is not meant to limit the same.

As described in preceding sections, the high-voltage generator disclosed by the present disclosure is based on a versatile power modular electronic system that allows adapting the design to the required output voltage and characteristics of the pulses, according to the specific application or treatment to provide.

Figure 1:
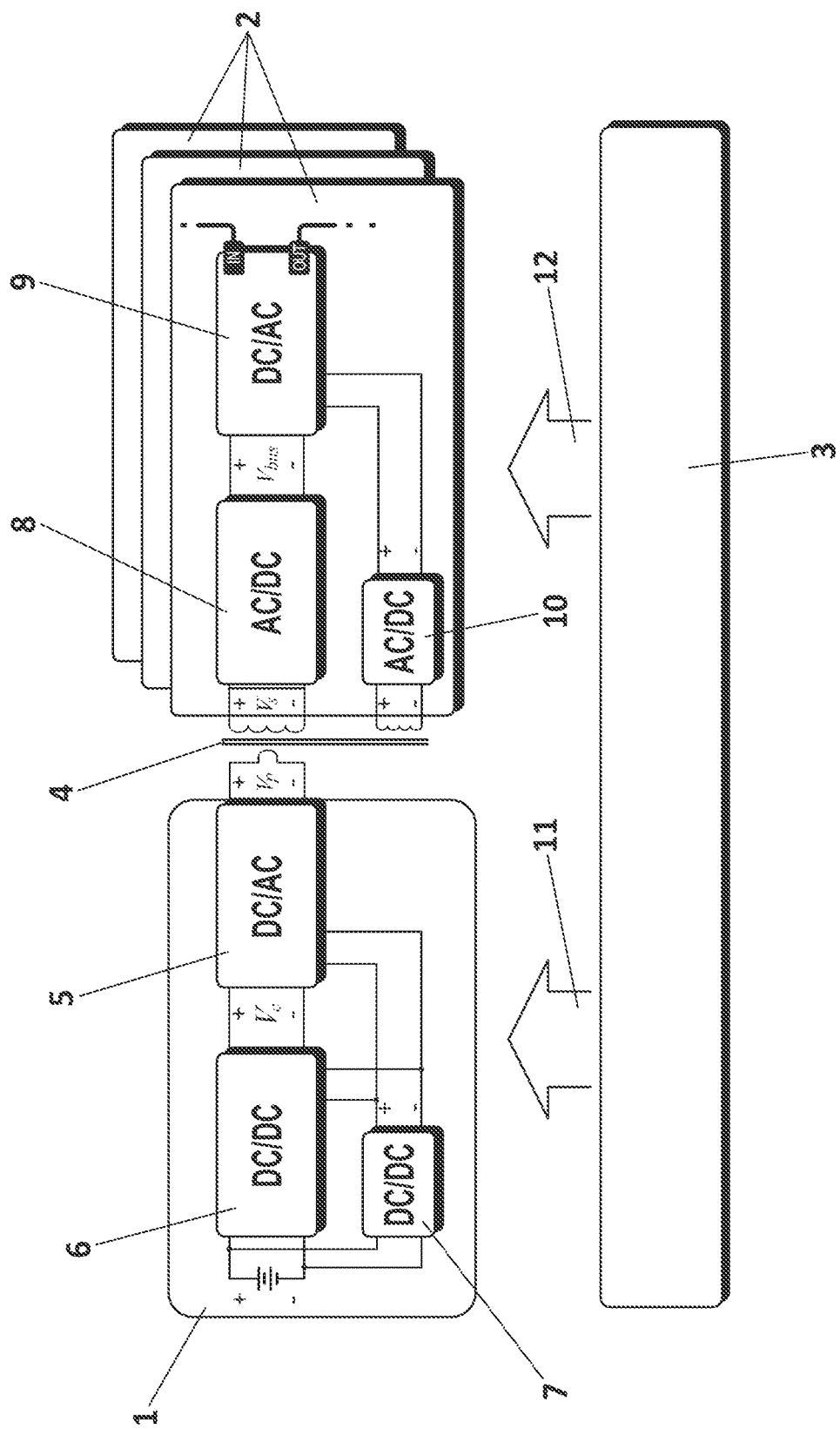
FIG. 1 shows a block diagram of the versatile power electronic modular system of the disclosure according to one or more embodiments thereof.

Said FIG. 1 shows the general block diagram for the modular electronic power system of the disclosure, where said system essentially comprises a charging unit (1), one or more pulse generation modules (2) with a rectifier-inverter configuration, and a control unit (3). The pulse generation modules (2) are connected to the charging unit (1) by magnetic coupling through an isolation transformer (4).

The charging unit (1) may include a high-frequency indirect DC/AC inverter (5) connected to a previous DC/DC step-up converter (6). The main purpose of said charging unit (1) is to charge each of the generator modules (2) at the required voltage with the isolation transformer (4) through which they are coupled. It should be noted that the coupling via the transformer (4) provides the required insulation (greater than 15 kV); moreover, due to the high operating frequency (typically 200 kHz), a compact implementation of the system is achieved.

In addition to the aforementioned elements, the charging unit (1) comprises an auxiliary DC/DC block (7) that provides a power supply voltage $V_{aux,p}$, to control the DC/AC inverter (5) and the DC/DC step-up converter (6).

In addition, the pulse generation modules (2), arranged in the secondary side of the system isolation transformer (4), are in charge of generating the output voltage applied during the electroporation treatment. Each module (2) may include an AC/DC rectifier (8) and a DC/AC inverter (9) based on a bridge configuration, in order to enable the generation of output voltage bipolar pulses at each module (2).

Analogously to the arrangement of elements of the charging unit (1), each pulse generation module (2) can comprise an AC/DC auxiliary block (10) that is also powered from the secondary side of the isolation transformer (4), in charge of generating the power supply voltages $V_{aux,s}$ of the AC/DC rectifier (8) and the DC/AC inverter (9).

The pulse generation modules (2) of the system of the disclosure can be connected to one another in series, providing an output voltage that is the sum of the voltages generated by each of the individual generation modules (2). Similarly, the modules can be connected in parallel such that the current delivered is the sum of the currents of each module. In this way the disclosure provides a variable power stage that can adapt to the needs of the treatment to be performed in order to generate the required voltages and currents.

As described above, the system of the disclosure also comprises a control unit (3) that controls the electronic power system comprised of the charging unit (1) and each of the pulse generation modules (2). The control signals of the generation modules (2) are emitted using a programmable logic device (FPGA) integrated in each control unit (3). It should be noted that the generation of control signals by FPGA increases the versatility and adaptability of the output voltage pulses to the treatment to be performed. This is not possible in current commercial systems, which have severe restrictions regarding the types of voltage pulses that can be generated.

As mentioned in preceding sections, the control unit (3) may be configured with a programming means for the number of active generation modules (2) of the system during the application of the pulses, thereby allowing to change quickly the magnitude of the pulses or pulse trains applied, configuring the shape thereof.

In addition, due to the strict insulation requirements imposed by use and safety regulations for electroporation devices, the control signals may be insulated by optic fibers (11,12).

Figure 2:
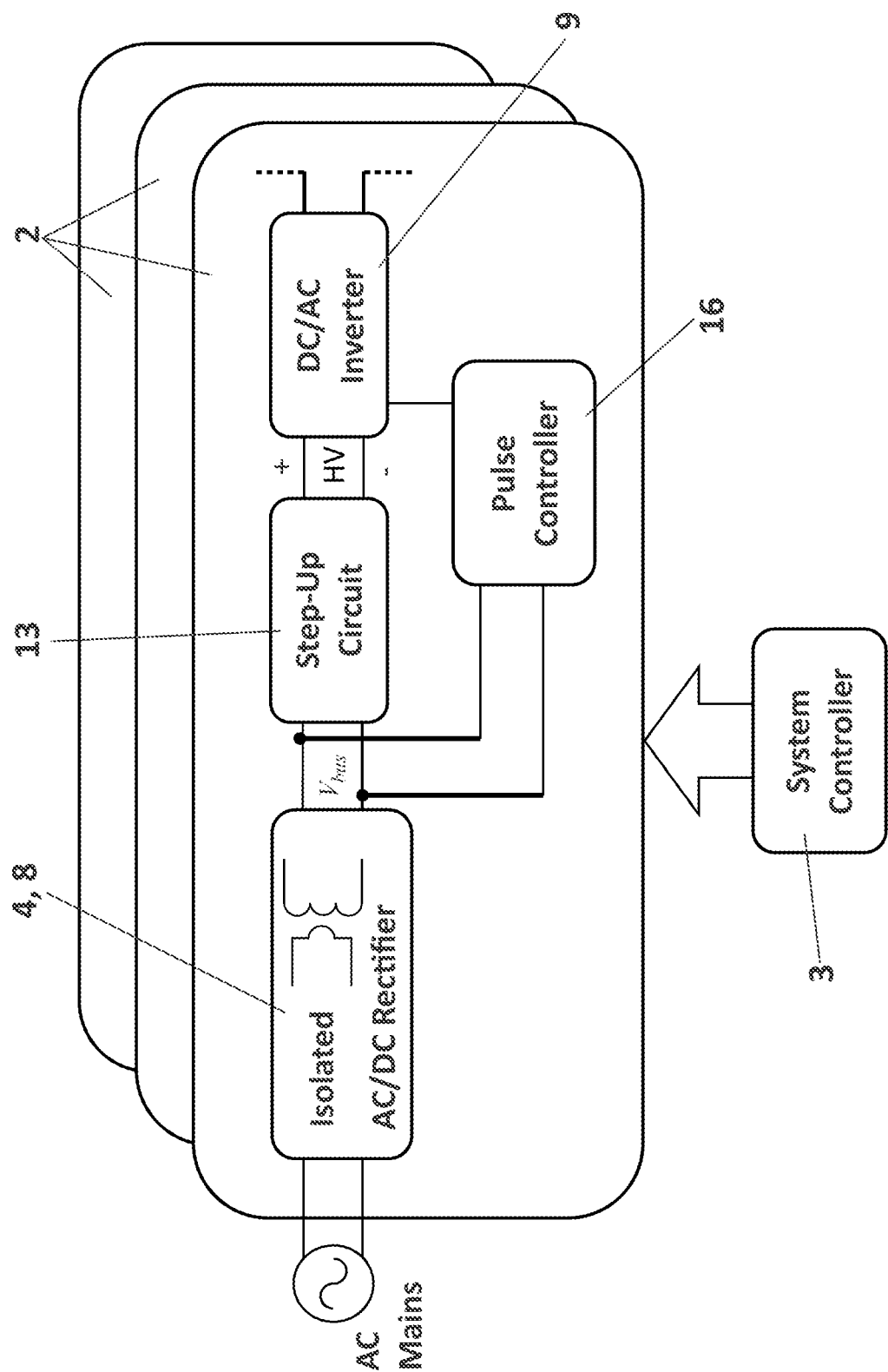
FIG. 2 shows a block diagram of the versatile power electronic modular system of the disclosure according to another embodiments thereof.

FIG. 2 represents an exemplary embodiment of variable power modular electronic system for generating unipolar or bipolar electrical pulses, wherein the system comprises two or more inter-connectable pulse generation modules (2) that can be electrically coupled to one another in parallel or in series, depending on the desired voltage and current output for each particular application. The two or more inter-connectable pulse generation modules (2), in use, generate the unipolar or bipolar electrical pulses such that when the two or more inter-connectable pulse generation modules (2) are coupled to one another in series an output voltage is a sum of individual output voltages of each pulse generation module, and when the two or more inter-connectable pulse generation modules (2) are coupled to one another in parallel a total output current is the sum of the current of each pulse generation module (2).

Each pulse generation module (2) also includes an isolated AC/DC rectifier (8) containing an isolation transformer (4), and a DC/AC inverter (9) having a bridge configuration, and preferably a step-up or step-down device (13) connected between the AC/DC rectifier (8) and the DC/AC inverter (8), so that the step-up or step-down device (13) can supply high voltage (HV) at the input of the DC/AC inverter (9). The DC/AC inverter (9) converts a DC voltage into the unipolar or bipolar electrical pulses.

Each pulse generation module (2) also includes a pulse controller (16), which in use, control activation and deactivation of the DC/AC inverter (9).

In a preferred embodiment the step-up or step-down device (13) includes a transformer and voltage multiplier.

The system also includes at least one system controller (3), programmed to control activation and deactivation of the pulse generation modules (2) to generate the unipolar or bipolar electrical pulses, and for varying at least one magnitude of the unipolar or bipolar electrical pulses. One or more system controllers (3) can be integrated into one or more pulse generation modules (2).

One or more parameters of the unipolar or bipolar electrical pulses includes at least one of: a polarity, an amplitude, a number, or a repetition frequency of the unipolar or bipolar electrical pulses.

The one or more system controllers (3) are coupled to the pulse generation modules (2) via direct, wireless, or optical connections.

Figure 3:
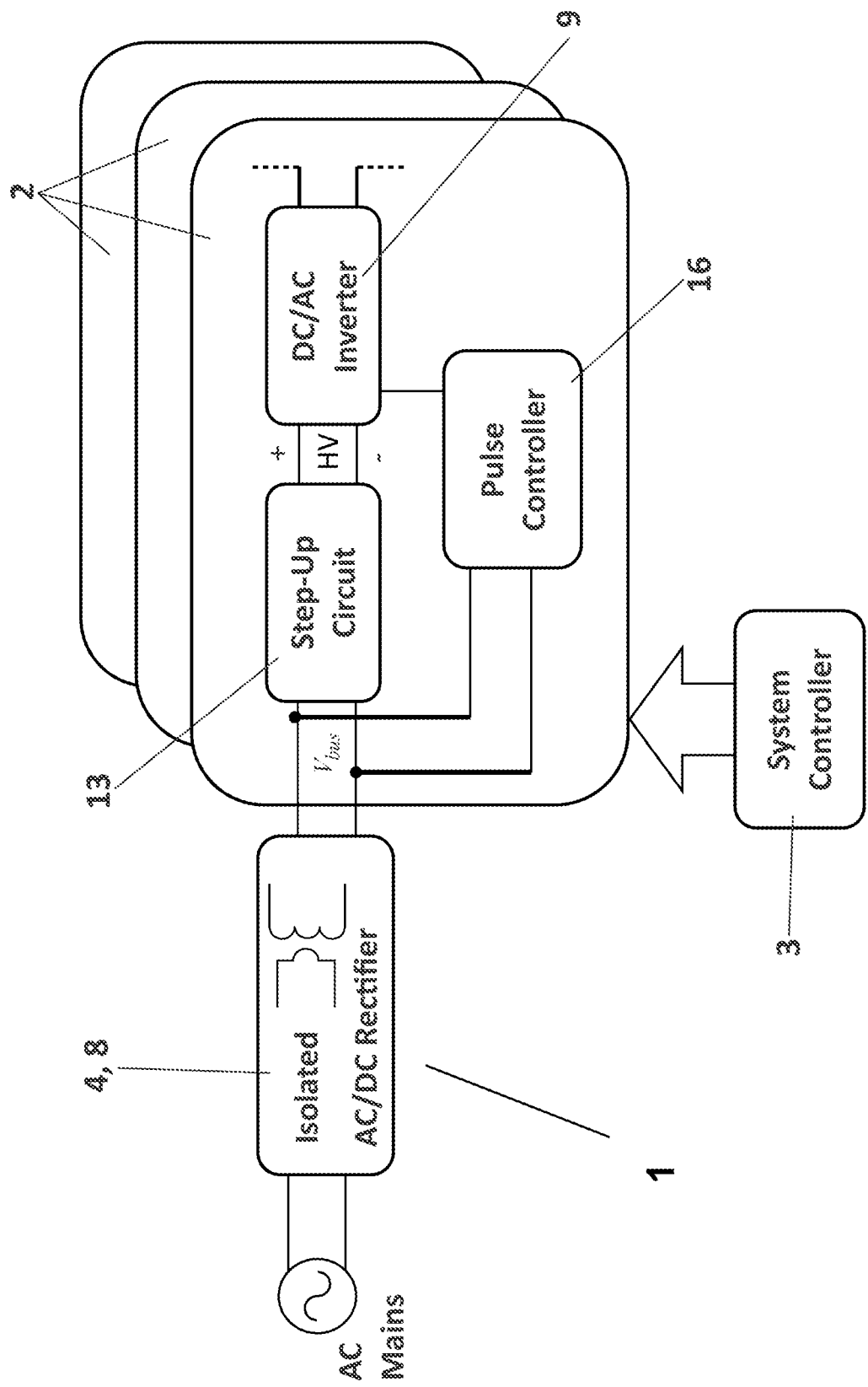
FIG. 3 shows a block diagram of the versatile power electronic modular system of the disclosure according to another embodiments thereof.

In the embodiment of FIG. 3, instead of having an individual AC/DC rectifier (8) for each module (2), the system includes a charging circuit (1) which, in use, charges or supplies power to all the pulse generation modules (2). The charging circuit (1) is fed from AC mains, and it includes an isolated AC/DC rectifier (8) in common for all the pulse generation modules (2). In this embodiment, each pulse generation module (2) comprises a step-up or step-down device (13) connected between the isolated AC/DC rectifier (8) and the DC/AC inverter (9), and a pulse controller (16).

The system controllers (3) can be implemented as one of: a field-programmable gate array (FPGA), configurable programmable logic device (CPLD), application-specific integrated circuit (ASIC), microcontroller, or a single-board computer.

The pulse controller (16) preferably is fed from the output of the AC/DC rectifier (8), and it is adapted to control activation and deactivation of the DC/AC inverter (9). Preferably, each pulse controller (16) includes drivers for the DC/AC inverter (9).

The pulse controllers (16) can be implemented as at least one of: field-programmable gate array (FPGA), configurable programmable logic device (CPLD), application-specific integrated circuit (ASIC), microcontroller, or a single-board computer.

Figure 4:
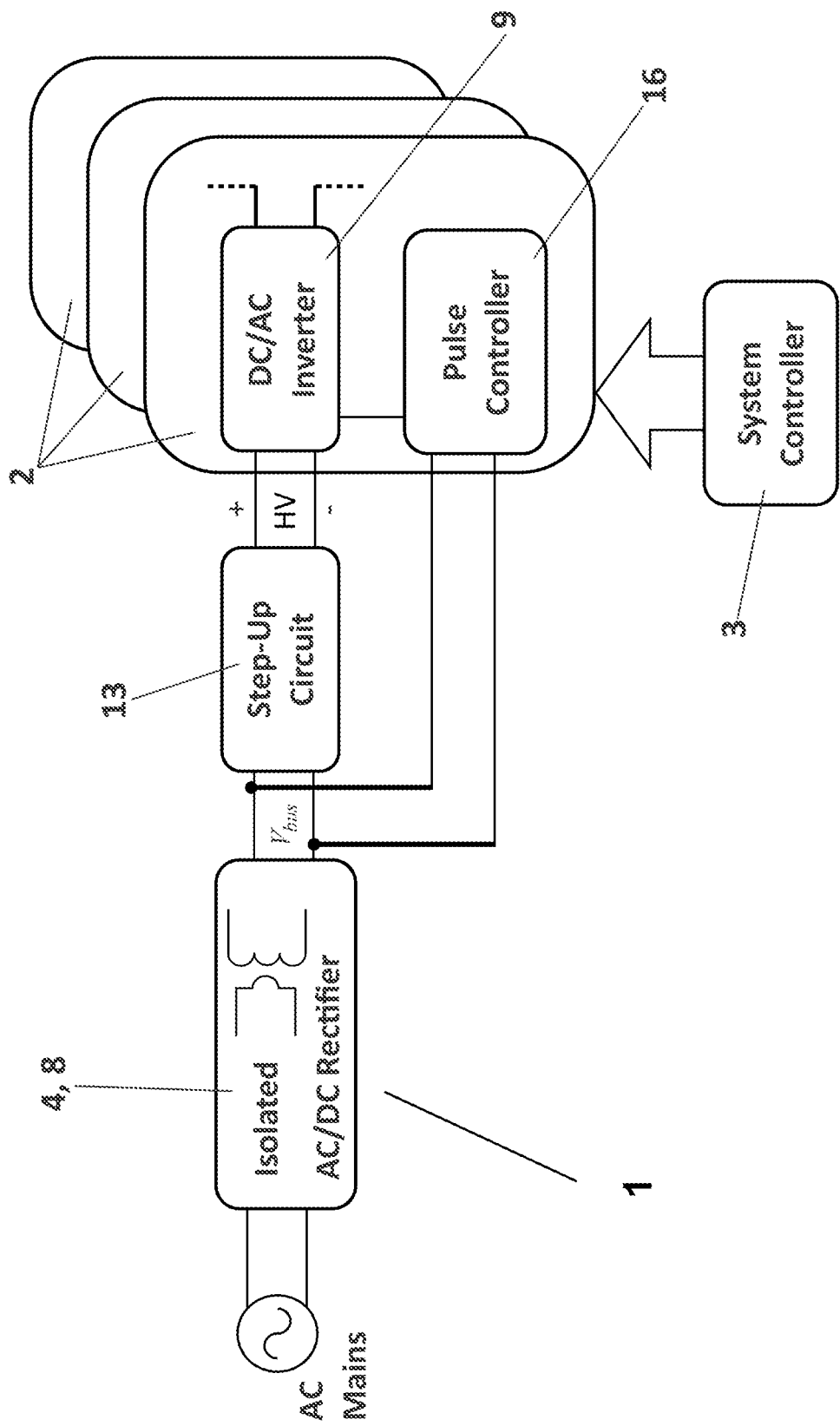
FIG. 4 shows a block diagram of the versatile power electronic modular system of the disclosure according to another embodiments thereof.

In the embodiment of FIG. 4, one step-up or step-down device (13) is also part of the charging circuit (1), such that all the modules (2) share, the common AC/DC rectifier (8) and a step-up or step-down device (13) coupled with the common isolated AC/DC rectifier (8), such that the pulse generation modules (2) are coupled to the common isolated AC/DC rectifier by means of the step-up or step-down device (13).

Figure 5:
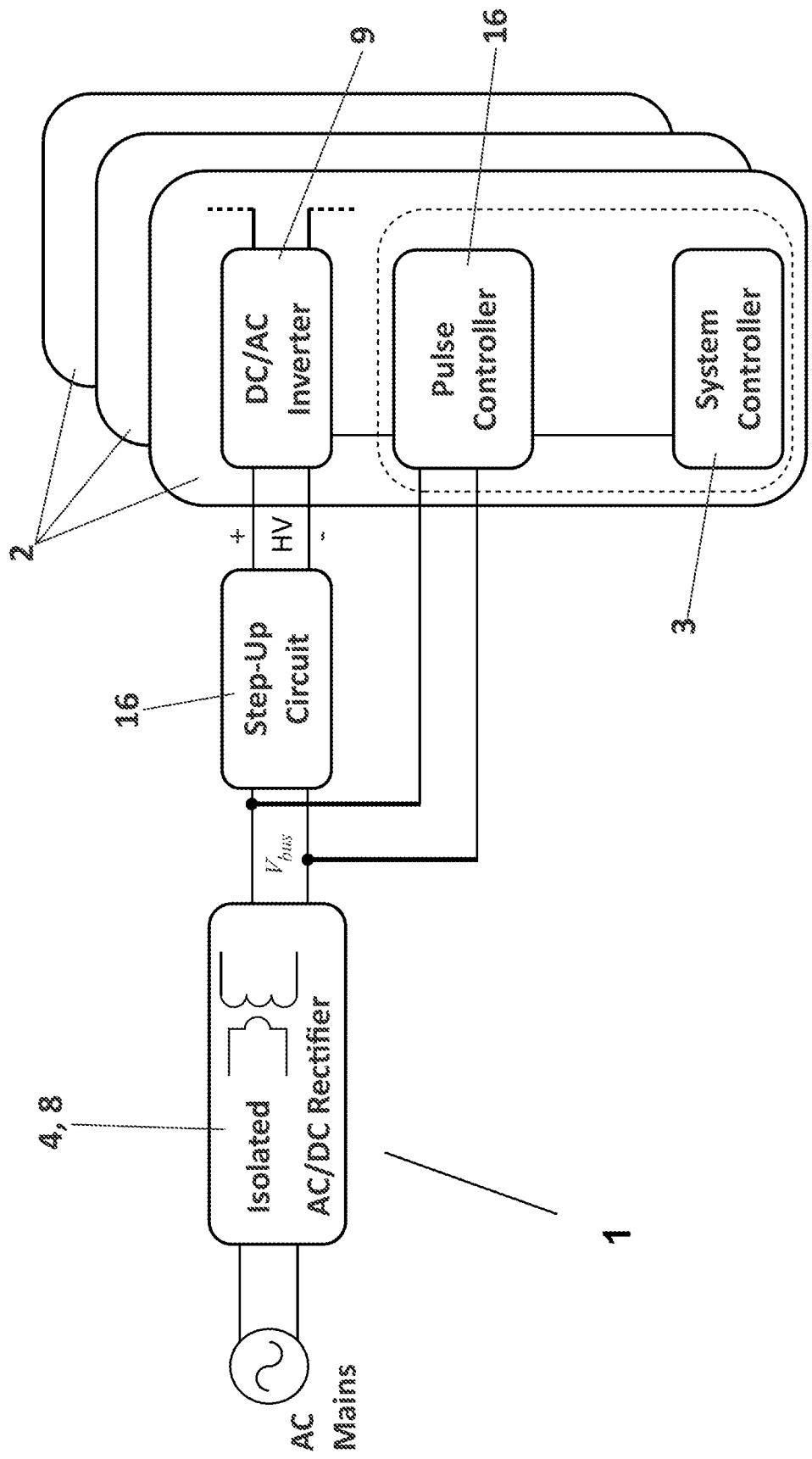
FIG. 5 shows a block diagram of the versatile power electronic modular system of the disclosure according to another embodiments thereof.

In the embodiment of FIG. 5, a system controller (3) is integrated in a pulse generation module (2).

Preferably, in the embodiments of FIGS. 2 to 5, the pulse controller (16) is communicated with system controller (3), and the system controller (3) is programmed to distribute instructions to the pulse generation module (2).

The system controller (3) is programmed, such that the amplitude between sequential unipolar or bipolar pulses is variable, based on the number of pulse generation modules (2) that are activated by a controller during a given pulse.

Preferably, the system is adapted for its use in electroporation applications.

In addition, the duration between sequential unipolar or bipolar pulses is variable based on the activation timing pattern created by the controller (3).

In a preferred embodiment, the controller (3) is programmed to set a unipolar or bipolar pulse duration within the range 10 nanoseconds to 1 millisecond.

In a preferred embodiment, the controller (3) is programmed to set a delay between unipolar or bipolar pulses within the range 10 nanoseconds to 100 milliseconds.

Figure 6:
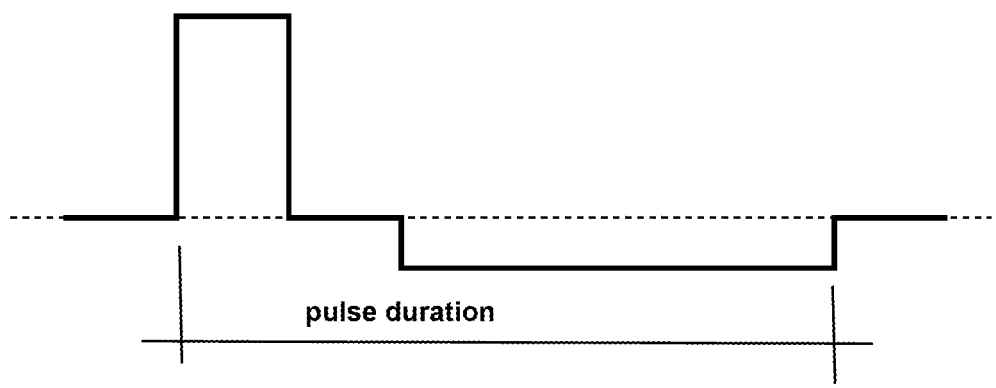
FIG. 6 shows an exemplary waveform of the output voltage/current, obtained by the interconnection of a two or more pulse generation modules.

FIG. 6 represents an exemplary waveform and pulse duration generated with the system of this disclosure. As shown in FIG. 6, the waveform is asymmetric and charge balanced, that is, positive and negative areas of the waveform have the same value. In the waveform, the initial high-voltage peak induce electroporation, and the subsequent lower-voltage prevent muscle/nerve stimulation.

In a preferred embodiment, the controller (3) is programmed such that in event that one or more of the pulse generation modules (2) fails in a short-circuit state, the remaining operable pulse generation modules (2) are switched open (turned-off) to block the output, so the total output voltage is null.

Figure 7:
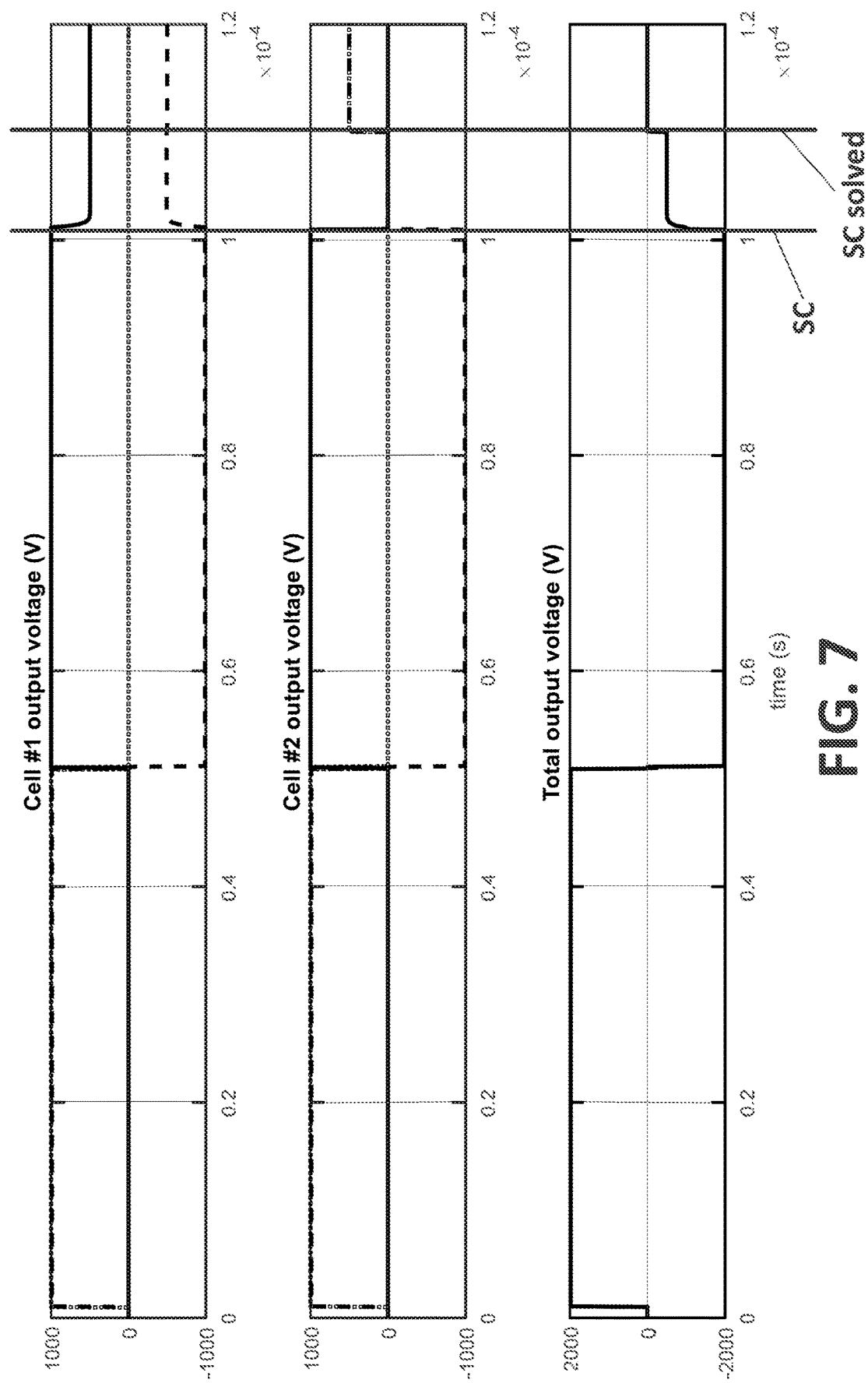
FIG. 7 shows a comparison of several output voltages generated by several pulse generation modules, and the behavior of the system when one of the modules is short circuited.

This feature of the system is illustrated in FIG. 7, wherein it is noted that when a short-circuit state (SC) of a pulse generation module (2) (Cell 1) is detected, remaining module (Cell 2) is turned-off (open circuit) to block the total output voltage (output voltage is null).

This short-circuit detection can be made either by hardware current comparison, or by software after processing measurements in the control unit.

For that purpose, at least one the pulse generation module (2) incorporates a current monitoring device, configured to detect in use a short-circuit state of any one of the pulse generation modules (2) and communicates the failure of a particular module (2) to the controller (3).

Finally, the system of the disclosure may communicate using wireless means, for example a WiFi network connected to a remote computer (not shown) through which the polarity, amplitude, number of pulses in each burst, number of bursts and repetition frequency thereof are configured.

The system of the disclosure provides satisfactory results in both treatment of plant tissues and treatment of live animal tissues.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A variable power modular electronic system for generating unipolar or bipolar electrical pulses, comprising:
   two or more inter-connectable pulse generation modules electrically coupled to one another in parallel or in series, the two or more inter-connectable pulse generation modules, in use, generate the unipolar or bipolar electrical pulses such that when the two or more inter-connectable pulse generation modules are coupled to one another in series, an output voltage is a sum of individual output voltages of each pulse generation module, and when the two or more inter-connectable pulse generation modules are coupled to one another in parallel, a total output current is the sum of the current of each pulse generation module;
   one or more AC/DC rectifiers coupled to electric mains and containing an isolation transformer, and
   wherein each of the pulse generation modules includes a DC/AC inverter having a bridge configuration and coupled with one AC/DC rectifier, wherein the DC/AC inverter, in use, outputs the unipolar or bipolar electrical pulses;
   a system controller, programmed to control activation and deactivation of the pulse generation modules for generating the unipolar or bipolar electrical pulses, and for varying at least one magnitude of the unipolar or bipolar electrical pulses.

2. The variable power modular electronic system according to claim 1, wherein at least one pulse generation module has an individual isolated AC/DC rectifier.

3. The variable power modular electronic system according to claim 1, comprising a common isolated AC/DC rectifier in common for the pulse generation modules, such that the pulse generation modules are coupled to the common isolated AC/DC rectifier.

4. The variable power modular electronic system according to claim 1, at least one step-up or step-down device connected between the common isolated AC/DC rectifier and the DC/AC inverter.

5. The variable power modular electronic system according to claim 4, wherein the step-up device includes a transformer and a voltage multiplier.

6. The variable power modular electronic system according to claim 1, wherein at least one pulse generation module comprises one or more pulse controllers, which in use, control activation and deactivation of the DC/AC inverter.

7. The variable power modular electronic system according to claim 6, wherein the pulse controller includes drivers for the DC/AC inverter.

8. The variable power modular electronic system according to claim 6, wherein the pulse controllers comprise a field-programmable gate array (FPGA), configurable programmable logic device (CPLD), application-specific integrated circuit (ASIC), microcontroller, single-board computer, or a combination thereof.

9. The variable power modular electronic system according to claim 6, wherein one system controller is further programmed to communicate with the pulse controller, and to distribute instructions to the pulse generation modules.

10. The variable power modular electronic system according to claim 1, wherein one or more system controllers comprise a field-programmable gate array (FPGA), configurable programmable logic device (CPLD), application-specific integrated circuit (ASIC), microcontroller, single-board computer, or a combination thereof.

11. The variable power modular electronic system according to claim 1, wherein one or more system controllers are integrated into one or more pulse generation modules.

12. The variable power modular electronic system according to claim 6, wherein a pulse controller and system controller are integrated into the same pulse generation module.

13. The variable power modular electronic system according to claim 1, wherein one or more system controllers are coupled to the pulse generation modules via direct, wireless, or optical connections.

14. The variable power modular electronic system according to claim 1, wherein the system controller is further programmed, such that the amplitude between sequential unipolar or bipolar pulses is variable based on the number of pulse generation modules that are activated by the system controller during a given pulse.

15. The variable power modular electronic system according to claim 1, wherein the system controller is further programmed, such that the duration between sequential unipolar or bipolar pulses is variable based on the activation timing pattern created by the system controller.

16. The variable power modular electronic system according to claim 1, wherein the system controller is programmed to set a unipolar or bipolar pulse duration within the range 10 nanoseconds to 1 millisecond.

17. The variable power modular electronic system according to claim 1, wherein the system controller is programmed to set a delay between unipolar or bipolar pulses within the range 10 nanoseconds to 100 millisecond.

18. The variable power modular electronic system according to claim 1, wherein one or more parameters of the unipolar or bipolar electrical pulses includes at least one of a polarity, an amplitude, a number, or a repetition frequency of the unipolar or bipolar electrical pulses.

19. The variable power modular electronic system according to claim 1, wherein the system controller is programmed such that in event that one or more of the pulse generation modules is short-circuited, the remaining operable pulse generation modules are switched open to block the output.

20. The variable power modular electronic system according to claim 19, wherein the pulse generation modules incorporate a current monitoring device, which in use detects a short-circuit state of the pulse generation modules.

21. The variable power modular electronic system according to claim 1, configured for its use in electroporation applications.

* * * * *